United States Patent
Changoer et al.

(10) Patent No.: US 10,842,786 B2
(45) Date of Patent: Nov. 24, 2020

(54) CHEWING GUM COMPOSITION COMPRISING CANNABINOIDS AND NICOTINE

(71) Applicant: APIRx Pharmaceutical USA, LLC, New York, NY (US)

(72) Inventors: Lekhram Changoer, Ridderkerk (NL); George Anastassov, New York, NY (US)

(73) Assignee: APIRx Pharmaceutical USA, LLC, New York, NY (US)

( * ) Notice: Subject to any disclaimer, the term of this patent is extended or adjusted under 35 U.S.C. 154(b) by 0 days.

(21) Appl. No.: 15/494,514

(22) Filed: Apr. 23, 2017

(65) Prior Publication Data

US 2017/0312261 A1    Nov. 2, 2017

Related U.S. Application Data

(60) Provisional application No. 62/328,467, filed on Apr. 27, 2016.

(51) Int. Cl.

| | | |
|---|---|---|
| *A61K 31/455* | (2006.01) |
| *A61K 47/38* | (2006.01) |
| *A61K 47/26* | (2006.01) |
| *A61K 47/10* | (2017.01) |
| *A61K 9/68* | (2006.01) |
| *A61K 47/02* | (2006.01) |
| *A61K 31/352* | (2006.01) |
| *A61K 31/05* | (2006.01) |
| *A61K 47/46* | (2006.01) |
| *A61K 47/12* | (2006.01) |
| *A61K 47/58* | (2017.01) |

(52) U.S. Cl.
CPC .......... *A61K 31/455* (2013.01); *A61K 9/0058* (2013.01); *A61K 31/05* (2013.01); *A61K 31/352* (2013.01); *A61K 47/585* (2017.08)

(58) Field of Classification Search
None
See application file for complete search history.

(56) References Cited

U.S. PATENT DOCUMENTS

| | | | | |
|---|---|---|---|---|
| 4,753,805 A | * | 6/1988 | Cherukuri | A23G 4/06 426/454 |
| 2003/0114475 A1 | * | 6/2003 | Fox | A61K 31/145 514/282 |
| 2010/0247586 A1 | * | 9/2010 | Hugerth | A23G 1/32 424/401 |
| 2011/0097283 A1 | * | 4/2011 | Van Damme | A61K 9/0058 424/48 |
| 2012/0263785 A1 | * | 10/2012 | Rossi | A61K 9/4858 424/451 |
| 2014/0302148 A1 | | 10/2014 | Winnicki | |
| 2015/0265636 A1 | * | 9/2015 | Kane | A61K 31/685 514/78 |
| 2016/0015683 A1 | * | 1/2016 | McCarty | A61J 3/007 206/528 |

* cited by examiner

*Primary Examiner* — Michael P Cohen
(74) *Attorney, Agent, or Firm* — Swidler Law Group, LLC; Sean S. Swidler

(57) ABSTRACT

A chewing gum composition comprising cannabinoids or derivatives thereof and nicotine in the form of nicotine polacrilex is provided. The chewing gum composition is formulated to provide rapid and controlled release of cannabinoids and nicotine during chewing. Methods to provide tobacco and/or *cannabis* smoking cessation using the chewing gum composition according to this invention are also provided.

14 Claims, 1 Drawing Sheet

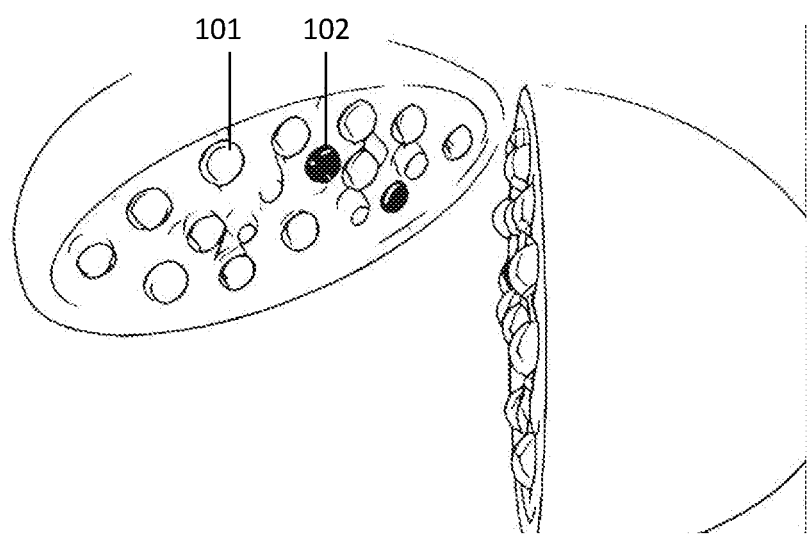

CHEWING GUM COMPOSITION COMPRISING CANNABINOIDS AND NICOTINE

BACKGROUND OF THE INVENTION

Field of the Invention

Smoking cessation is a developing area with many proposed techniques and remedies. This invention proposes a chewing gum composition with cannabinoids and nicotine to provide a smoking cessation means.

Description of the Related Technology

Nicotine gum is a chewing gum with nicotine, which delivers nicotine to the body via absorption by tissues of the mouth. Nicotine gum is used as an aid in nicotine replacement therapy. Individuals smoking tobacco with nicotine may wish to wean themselves of smoking tobacco and nicotine delivered by the means of a chewing gum is a replacement therapy to reduce the harmful effect of inhaling tobacco smoke.

The *cannabis* plant has many naturally occurring substances that are of great interest in the fields of science and medicine. Isolated compounds from the *cannabis* plant include $\Delta^9$-tetrahydrocannabinol (THC), cannabinoid (CBD), cannabichromene (CBC), cannabigerol (CBG), cannabidivarin (CBDV), among other compounds. While THC has psychoactive effects, CBD, CBC, CBG, and CBDV do not. Isolated compounds from the *cannabis* plant are called cannabinoids. There are a total of one hundred and forty (140) cannabinoids that have been isolated from the *cannabis* plant. Many researchers have confirmed the medicinal value of cannabinoids. Cannabinoids have been investigated for possible treatment of seizures, nausea, vomiting, lack of appetite, pain, arthritis, inflammation, and other conditions.

The IUPAC nomenclature of THC is (−)-(6aR,10aR)-6,6,9-trimethyl-3-pentyl-6a,7,8,10a-tetrahydro-6H-benzo[c]chromen-1-ol. CBD's IUPAC nomenclature is 2-((1S,65)-3-methyl-6-(prop-1-en-2-yl)cyclo-hex-2-enyl)-5-pentylbenzene-1,3-diol). CBC has the IUPAC nomenclature of 2-methyl-2-(4-methylpent-3-enyl)-7pentyl-5-chromenol. These are among the most prominent compounds in the family of compounds extracted from the *cannabis* plant referred to as cannabinoids.

Cannabinoids may be isolated by extraction or cold pressing of *cannabis* plants. Plants in the *cannabis* genus include *Cannabis sativa*, *Cannabis ruderalis*, and *Cannabis indica*. These plants are the natural sources of cannabinoids. Cannabinoids are also available in synthetic forms. Methods to synthesize cannabinoids in lab settings were discovered and are still currently practiced. Synthetic cannabinoids are more targeted, in that the synthetic compound usually comes isolated without other cannabinoids mixed in.

Cannabinoids from hemp are marketed in the United States. Various products containing cannabinoids have been marketed in recent years. Cannabinoids may be consumed by ingestion, by inhalation, or by transdermal delivery.

There are individuals who smoke *cannabis* mixed with tobacco and others who smoke pure dry *cannabis* plant materials concurrently with tobacco. In both groups there are individuals who are dependent on the active ingredients of *cannabis* but would like to quit. There are individuals who smoke *cannabis* but are aware of the deleterious effects of smoking on the respiratory tract and general health. However, these individuals may smoke *cannabis* for medical indications (chemotherapy related cachexia, AIDS related cachexia, chronic neuropathic pain, etc.) and would like to wean themselves from smokeable *cannabis* and entertain other forms of delivery.

There exists a demand for a product to replace nicotine while reducing nicotine craving. There exists another demand for a product to replace *cannabis* smoking dependence, which may be concurrent with tobacco smoking dependence.

ABBREVIATIONS

CBC: cannabichromene
CBD: cannabidiol
CBG: cannabigerol
CBDV: cannabidivarin
THC: $\Delta^9$-tetrahydrocannabinol

SUMMARY

The present invention relates to a chewing gum composition comprising cannabinoids or derivatives thereof and nicotine, which may be provided in encapsulated form or by a delivery mechanism. This invention further relates to the use of this chewing gum composition in advancing tobacco smoking cessation and concurrent *cannabis* and tobacco smoking cessation.

There is provided a chewing gum composition comprising, based on total weight of the composition:
  0.1 to 1% by weight of at least one cannabinoid;
  0.3 to 1% by weight of nicotine polacrilex;
  25 to 95% by weight of a gum base;
  1 to 10% by weight of at least one flavoring agent selected from the group consisting of peppermint, cinnamon, watermelon, and spearmint; and
  1 to 35% by weight of at least one sweetening agent selected from the group consisting of isomalt, sorbitol, stevia, maltitol, and xylitol.

There is further provided a chewing gum composition according to the above, wherein the at least one cannabinoid is provided in combination with suitable carriers selected from the group consisting of microcrystalline cellulose derivatives, sugar alcohol, dextran, agarose, agar, pectin, alginate, xanthan, chitosan, and starch.

There is further provided a chewing gum composition according to the above, wherein the at least one cannabinoid is provided in encapsulated form.

There is further provided a chewing gum composition according to the above, wherein the encapsulated form comprises beads formed from a cannabinoid and liquid excipient emulsion absorbed into silica gel or an edible polymer.

There is further provided a chewing gum composition according to the above, wherein the at least one cannabinoid is cannabidiol, $\Delta^9$-tetrahydrocannabinol, cannabichromene, cannabigerol, cannabidivarin, derivatives thereof, or their acid metabolites.

There is provided a chewing gum composition according to the above, further comprising at least one softener present at 2 to 7% by weight of the chewing gum composition.

There is provided a chewing gum composition according to the above, wherein the softener is glycerine.

There is provided a chewing gum composition according to the above, further comprising of at least one buffering agent selected from the group consisting of acetates, glycinates, phosphates, carbonates, glycerophosphates, citrates, and borates.

There is provided a chewing gum composition according to the above, wherein the at least one buffering agent is present at 0.5 to 5% by weight of the chewing gum composition.

There is provided a chewing gum composition according to the above, further comprising at least one preservative.

There is further provided a chewing gum composition according to the above, wherein the preservative is citric acid.

There is provided a chewing gum composition according to the above, further comprising at least one pharmaceutically acceptable excipient selected from the group consisting of fillers, disintegrants, binders, and lubricants.

There is provided a chewing gum composition according to the above, further comprising silicon dioxide or magnesium stearate.

There is provided a chewing gum composition according to the above, further comprising at least one anti-oxidant selected from the group consisting of ascorbyl palminate and sodium ascorbate.

There is provided a chewing gum composition according to the above, further comprising water.

There is provided a method to treat or alleviate tobacco smoking in a mammal in need thereof, comprising administering to the mammal a chewing gum composition according to the above.

There is provided a method as above, wherein the mammal receives the chewing gum administration 1 to 12 times a day.

There is provided a method to treat or alleviate tobacco smoking concurrent with *cannabis* smoking in a mammal in need thereof, comprising administering to the mammal a chewing gum composition according to the above.

There is provided a method as above, wherein the mammal receives the chewing gum administration 1 to 12 times a day.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1 is the perspective view of the chewing gum composition's cross section showing various beads inside, according to embodiments of this invention.

DETAILED DESCRIPTION OF CERTAIN INVENTIVE EMBODIMENTS

Embodiments of this application relate to a chewing gum composition comprising cannabinoids or derivatives thereof and nicotine. The chewing gum composition may be consumed by a human for smoking cessation.

According to embodiments, the chewing gum composition comprises 0.1-1% by weight of at least one cannabinoid or derivatives thereof based on total weight of the composition. In a 2 g chewing gum piece, the at least one cannabinoid or derivatives thereof may comprise 2-20 mg.

Cannabinoids and derivatives thereof as in these embodiments may be $\Delta^9$-tetrahydrocannabinol (THC), cannabichromene (CBC), cannabigerol (CBG), cannabidivarin (CBDV), cannabidiol (CBD), derivatives thereof, their acid metabolites, or a combination of cannabinoids and/or their acid metabolites.

Cannabinoids and derivatives thereof may be provided in a solid material composed of an edible solid, such as a sugar alcohol, to prevent binding with the gum base. Alternatively, cannabinoids and derivatives thereof may be provided in a granule embedded into the gum matrix. Cannabinoids and derivatives provided in these manners may improve cannabinoid release during mastication of the chewing gum according to embodiments.

In embodiments, suitable carriers may be provided in combination with cannabinoids and derivatives thereof. The carriers may be insoluble in water or has a very low solubility, lower than 1% w/w in water at 25° C. Insolubility may prevent cannabinoid contents from migrating out of the carrier due to environment moisture.

Suitable carriers may be combined with cannabinoid and derivatives thereof before inclusion into the gum matrix may include certain cellulose, such as microcrystalline cellulose derivatives such as hemicellulose, certain polysaccharide, such as dextran, agarose, agar, pectin, alginate, xanthan, chitosan, or starch, among other suitable polysaccharides. These carriers may be synthetic, semi-synthetic, or of natural origin. The combination of cannabinoids and derivatives thereof and suitable carriers may result in cannabinoids and derivatives thereof being present within internal voids of these carriers.

Suitable microcrystalline cellulose may be selected from the group consisting of AVICEL® grades PH-100, PH-102, PH-103, PH-105, PH-112, PH-113, PH-200, PH-300, PH-302, VIVACEL® grades 101, 102, 12, 20 and EMOCEL® grades 50M and 90M, and the like, and mixtures thereof. Internal voids of these carriers are particularly useful in carrying cannabinoids and derivatives thereof or their acid metabolizes.

In embodiments, cannabinoids and derivatives thereof may be provided in encapsulated form, such as by cannabinoids and derivatives thereof in liquid excipients and absorbed in an edible polymer or silicagel forming beads with a size of 10-50 μm diameter. Other methods to encapsulate cannabinoids and derivatives thereof may be suitable.

Cannabinoids and derivatives thereof may be provided in a granule which may be coated with at least one layer to protect the granule. Cannabinoids and derivatives thereof provided in coated granule may enable controlled release profiled of cannabinoids and derivatives thereof.

In embodiments, nicotine may be provided as a complex with methacrylic acid polymer and divinylbezene, forming nicotine polacrilex. The use of polymer as a delivery system maximizes the amount of nicotine released and absorbed by the oral mucosa. Nicotine polacrilex may be present in the chewing gum composition at 0.3-1% by weight based on the total weight composition. In a 2 g chewing gum piece, nicotine polacrilex may comprise 6-20 mg. Nicotine comprises approximately 33% weight mass of nicotine polacrilex and thus the chewing gum composition may be formulated accordingly for desired nicotine content. Typically, chewing gum compositions may be produced in two (2) dosages: a chewing composition with 2 mg nicotine, among other ingredients; or a chewing composition with 4 mg nicotine, among other ingredients.

FIG. 1 illustrates a chewing gum composition according to embodiments, wherein cannabinoids and derivatives thereof in encapsulated form may be present in the gum body as micro-beads 101 formed from a method described herein. Nicotine polacrilex may be present in different micro-beads 102.

The chewing gum composition according to embodiments may comprise a gum base, which is the matrix wherein other ingredients may be provided. Gum base used in these embodiments may be non-disintegrating. Gum base such as Gum powder PG 11 TA, Gum powder PG 11 TA New, Gum powder PG 5 TA, Gum powder PG 5 TA New, or Gum powder PG N12 TA, among other suitable gum bases, may be used. A combination of gum bases may be suitable to embed other ingredients. Gum base may comprise 25-95% by weight of the chewing gum composition according to embodiments.

In embodiments, the chewing gum composition may further comprise other ingredients, including but not limited to buffering agents, emulsifiers, waxes, fats, oils, plasticizers, sweetening agents, flavoring agents, anti-oxidants, preservatives, and the likes.

In embodiments, buffering agents may be included in this chewing gum composition according to embodiments. Suitable buffering agents may include acetates, glycinates, phosphates, carbonates, glycerophosphates, citrates, borates, mixtures thereof, or other suitable buffering agents. Buffering agents may be present at 0.5-5% by weight.

The chewing gum composition according to embodiments may have other ingredients to improve organoleptic properties. Ingredients such as certain flavoring agents or certain sweetening agents may be included. Flavoring agents may include peppermint, spearmint, cinnamon, watermelon, eucalytus, menthol, or other suitable flavoring agents. Flavoring agents may be present in this chewing composition at 1-10% by weight.

In embodiments, sweetening agents may include certain sugar alcohol such as isomalt, sorbitol, maltitol, stevia, xylitol, certain artificial sweetening agents, such aspartame, sucralose, acesulfame potassium or saccharin, and/or certain sugar such as dextrose, sucrose, maltose, fructose, or other suitable sweetening agents. Sweetening agents may be present at 1-35% by weight of the chewing gum composition according to embodiments. Food colorants may be included in suitable quantity. Certain food colorants may be included to improve the aesthetic appearance of the chewing gum composition.

The chewing gum composition according to embodiments may comprise ingredients for preservation such as citric acid. Additional ingredients to assist with powder flow and prevent the gum base from sticking to manufacturing surfaces may be included. Such ingredients may be silicon dioxide, stearates such as magnesium stearate, or talc. Other suitable ingredients for preservation and manufacturing management may be used.

Additional pharmaceutically acceptable excipients used in the chewing gum composition according to embodiments may be fillers, disintegrants, binders, or lubricants. Suitable fillers may be celluloses and cellulose derivatives including microcrystalline cellulose, hydroxypropylcellulose and sodium carboxymethylcellulose, lactose, starches including potato starch and corn starch. The chewing gum composition according to embodiments may further comprise at least one pharmaceutically acceptable excipient.

In embodiments, the chewing gum composition may further comprise an anti-oxidant. Anti-oxidants such as ascorbyl palminate and sodium ascorbate may also be included. Suitable lubricants may be added, including stearates including magnesium stearate, talc, silicon dioxide, and colloidal silica dioxide.

In embodiments, the chewing gum composition may further comprise ingredients to soften the gum body such as glycerine or certain fats. Softeners may be present in this chewing gum composition at 2-7% by weight of the chewing gum composition.

According to embodiments, the chewing gum composition may be coated or not coated. Coating materials may enable an aesthetic appeal while improving the organoleptic properties of the chewing gum composition according to embodiments.

According to embodiments, water may be present in this chewing gum composition to aid with the manufacturing process. Water used this in manufacturing process is of food quality.

The chewing gum composition according to embodiments may be made by conventional chewing gum production methods, such as a compressing process or by a hot process. In the compressing process, ingredients are mixed and compressed into the gum base using a compress machine. In the hot process, ingredients are mixed and heated in different steps before the gum base is poured in. The gum mixture is then molded and left to cure.

The chewing gum composition according to embodiments may be used for tobacco smoking cessation. Tobacco smoking may be treated or alleviated by consumption of chewing gums according to embodiments. A mammal, such as a human being, may chew the chewing gum composition 1-12 times a day to alleviate the nicotine craving sensation.

The chewing gum composition according to embodiments may be used for *cannabis* smoking cessation concurrent with tobacco smoking cessation. *Cannabis* smoking concurrent with tobacco smoking may be treated or alleviated by consumption of chewing gums according to embodiments. A mammal, such as a human being, may chew the chewing gum composition 1-12 times a day to aid nicotine and/or $\Delta^9$-THC craving sensation whiling curbing this craving.

EXAMPLES

Example 1

|     | Raw material | Percentage (%) |
| --- | --- | --- |
| A1  | Isomalt | 28.49 |
| A2  | CBD (encapsulated) | 0.5 |
| A3  | Microcrystalline cellulose | 0.5 |
| A4  | Nicotine polacrilex | 0.6 |
| B1  | Gum base | 24.5 |
| B2  | Sorbitol | 10 |
| B3  | Maltitol | 10 |
| B4  | Citric acid | 0.5 |
| B5  | Magnesium stearate | 2 |
| B6  | Silicon dioxide | 0.4 |
| B7  | Xylitol | 13.45 |
| B8  | *Stevia* | 1.05 |
| B9  | Peppermint | 4 |
| B10 | Spearmint | 4 |
| B11 | Colorants FD&C blue | 0.01 |
|     | Total | 100 |

Step 1: Make a blend of A1, A2, A3 and A4 to form Phase 1

Step 2: Mix B1-B11 in a separate vessel to form Phase 2

Step 3: Use a double layer chewing gum machine to compress Phase 1 and Phase

Example 2

| | Raw material | Percentage (%) |
|---|---|---|
| A1 | Gum base | 74.8 |
| A2 | Xylitol | 14 |
| A3 | Glycerine | 4.5 |
| B1 | Sacharrine | 0.4 |
| B2 | H20 | 1.5 |
| B3 | Nicotine polacrilex | 0.3 |
| B4 | Citric acid | 0.5 |
| C1 | Peppermint aroma oil | 1.5 |
| A4 | Peppermint powder | 1.5 |
| C2 | CBD (encapsulated) | 0.5 |
| A5 | Microcrystalline cellulose | 0.5 |
| | Total | 100 |

Step 1: Heat the gum base (A1) to 90° C., then add A2-A5 to form Phase 1

Step 2: Dissolve B1 and B4 in B2 to form Phase 2

Step 3: Heat the peppermint oil (C1) to 60-70° C., then add C2 and B3 to form Phase 3

Step 4: Add Phase 2 to Phase 1, stir vigorously and add Phase 3, stir for 7 minutes Step 5: Pour the gum mixture out and prepare chewing gum tablets by molding as needed.

Variations and modifications will occur to those of skill in the art after reviewing this disclosure. The disclosed features may be implemented, in any combination and sub-combination (including multiple dependent combinations and sub-combinations), with one or more other features described herein. The various features described or illustrated above, including any components thereof, may be combined or integrated in other systems. Moreover, certain features may be omitted or not implements.

Examples of changes, substitutions, and alterations are ascertainable by one skilled in the art and could be made without departing from the scope of the information disclosed herein. All references cited are hereby incorporated by reference herein in their entireties and made part of this application.

What is claimed is:

1. A method to treat or alleviate tobacco smoking in a mammal in need thereof, comprising administering to the mammal a chewing gum composition comprising:
   0.1 to 1% by weight of at least one cannabinoid;
   0.3 to 1% by weight of nicotine polacrilex;
   25 to 95% by weight of a gum base;
   1 to 10% by weight of at least one flavoring agent selected from the group consisting of peppermint, cinnamon, watermelon, and spearmint; and
   1 to 35% by weight of isomalt,
   wherein the at least one cannabinoid is provided in encapsulated form, and
   wherein the encapsulated form comprises beads formed from a cannabinoid and liquid excipient emulsion absorbed into silica gel.

2. The method of claim 1, wherein the mammal receives the chewing gum administration 1 to 12 times a day.

3. The method of claim 1, wherein the at least one cannabinoid is provided in combination with microcrystalline cellulose derivatives.

4. The method of claim 1, wherein the at least one cannabinoid is cannabidiol.

5. The method of claim 1, wherein the chewing gum composition further comprises at least one softener present at 2 to 7% by weight of the chewing gum composition.

6. The method of claim 5, wherein the softener is glycerin.

7. The method of claim 5, wherein the chewing gum composition further comprises at least one buffering agent selected from the group consisting of acetates, glycinates, phosphates, carbonates, glycerophosphates, citrates, and borates.

8. The method of claim 7, wherein the at least one buffering agent is present at 0.5 to 5% by weight of the chewing gum composition.

9. The method of claim 7, wherein the chewing gum composition further comprises at least one preservative.

10. The method of claim 9, wherein the preservative is citric acid.

11. The method of claim 9, wherein the chewing gum composition further comprises at least one pharmaceutically acceptable excipient selected from the group consisting of fillers, disintegrants, binders, and lubricants.

12. The method of claim 11, wherein the chewing gum composition further comprises silicon dioxide or magnesium stearate.

13. The method of claim 12, wherein the chewing gum composition further comprises at least one anti-oxidant selected from the group consisting of ascorbyl palmitate and sodium ascorbate.

14. The method of claim 13, wherein the chewing gum composition further comprises water.

* * * * *